United States Patent [19]

Clauss et al.

[11] Patent Number: 4,607,100

[45] Date of Patent: Aug. 19, 1986

[54] PROCESS FOR THE PREPARATION OF 6-METHYL-3,4-DIHYDRO-1,2,3-OXATHIA-ZIN-4-ONE 2,2-DIOXIDE AND ITS NON-TOXIC SALTS

[75] Inventors: Karl Clauss, Kelkheim; Adolf Linkies, Frankfurt am Main; Dieter Reuschling, Butzbach, all of Fed. Rep. of Germany

[73] Assignee: Hoechst Aktiengesellschaft, Frankfurt, Fed. Rep. of Germany

[21] Appl. No.: 714,177

[22] Filed: Mar. 20, 1985

[30] Foreign Application Priority Data

Mar. 22, 1984 [DE] Fed. Rep. of Germany ....... 3410439

[51] Int. Cl.$^4$ .......................................... C07D 291/06
[52] U.S. Cl. ......................................................... 544/2
[58] Field of Search ............................................. 544/2

[56] References Cited

U.S. PATENT DOCUMENTS

| | | | |
|---|---|---|---|
| 3,689,486 | 9/1972 | Clauss et al. | 544/2 |
| 3,926,976 | 12/1975 | Clauss et al. | 544/2 |
| 3,968,106 | 7/1976 | Clauss et al. | 544/2 |
| 3,968,107 | 7/1976 | Clauss et al. | 544/2 |
| 4,563,521 | 1/1986 | Clauss et al. | 544/2 |

*Primary Examiner*—John M. Ford
*Attorney, Agent, or Firm*—Curtis, Morris & Safford

[57] ABSTRACT

6-Methyl-3,4-dihydro-1,2,3-oxathiazin-4-one 2,2-dioxide is prepared by (a) reacting, in an inert organic solvent, a salt of sulfamic acid, which is at least partially soluble therein, with at least approximately the equimolar amount of an acetoacetylating agent, in the presence of an amine or phosphine catalyst, and by cyclizing the acetoacetamide-N-sulfonate which is formed in this reaction, or the free sulfonic acid, (b) by the action of at least approximately the equimolar amount of $SO_3$, where appropriate in an inert inorganic or organic solvent, to give 6-methyl-3,4-dihydro-1,2,3-oxathiazin-4-one 2,2-dioxide, which is produced in the form of the acid in this reaction;

it is possible, if desired, to obtain from the acid form (c) the appropriate salts by neutralization with bases.

The non-toxic salts—in particular the potassium salt—are valuable synthetic sweeteners.

14 Claims, No Drawings

PROCESS FOR THE PREPARATION OF 6-METHYL-3,4-DIHYDRO-1,2,3-OXATHIAZIN-4-ONE 2,2-DIOXIDE AND ITS NON-TOXIC SALTS

6-Methyl-3,4-dihydro-1,2,3-oxathiazin-4-one 2,2-dioxide is the compound of the formula

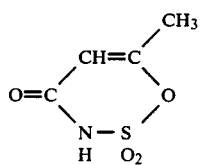

As a consequence of the acidic hydrogen on the nitrogen atom, the compound is able to form salts (with bases). The non-toxic salts, such as, for example, the Na, the K and the Ca salt, can, because of their sweet taste, which is intense in some cases, be used as sweeteners in the foodstuffs sector, the K salt ("Acesulfame K" or just "Acesulfame") being of particular importance.

A number of different processes is known for the preparation of 6-methyl-3,4-dihydro-1,2,3-oxathiazin-4-one 2,2-dioxide and its non-toxic salts; see Angewandte Chemie 85, Issue 22 (1973) pages 965 to 73, corresponding to International Edition Vol. 12, No. 11 (1973), pages 869–76. Virtually all the processes start from chloro- or fluorosulfonyl isocyanate (XSO₂NCO with X=Cl or F). The chloro- or fluorosulfonyl isocyanate is then reacted with monomethylacetylene, acetone, acetoacetic acid, tert.-butyl acetoacetate or benzyl propenyl ether (usually in a multistage reaction) to give acetoacetamide-N-sulfonyl chloride or fluoride which, under the action of bases (such as, for example, methanolic KOH), is cyclized and provides the corresponding salts of 6-methyl-3,4-dihydro-1,2,3-oxathiazin-4-one 2,2-dioxide. Where desired, the free oxathiazinone can be obtained from the salts in a customary manner (with acids).

Another process for the preparation of the oxathiazinone intermediate acetoacetamide-N-sulfonyl fluoride starts from sulfamoyl fluoride H₂NSO₂F, which is the partial hydrolysis product of fluorosulfonyl isocyanate (German Offenlegungsschrift No. 2,453,063). The fluoride of sulfamic acid H₂NSO₂F is then reacted with an approximately equimolar amount of the acetoacetylating agent diketene, in an inert organic solvent, in the presence of an amine, at temperatures between about −30° and 100° C.; the reaction takes place in accordance with the following equation (with triethylamine as the amine):

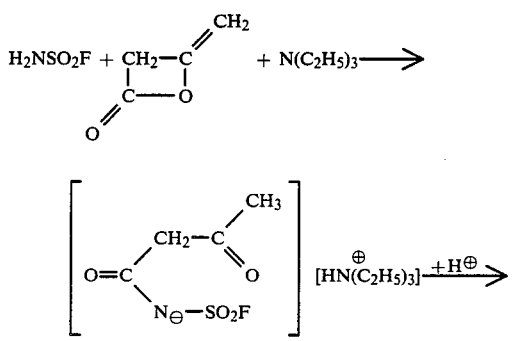

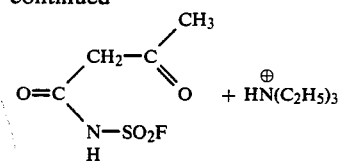

The acetoacetamide-N-sulfonyl fluoride is then cyclized in a customary manner using a base, for example using methanolic KOH, to the sweetener:

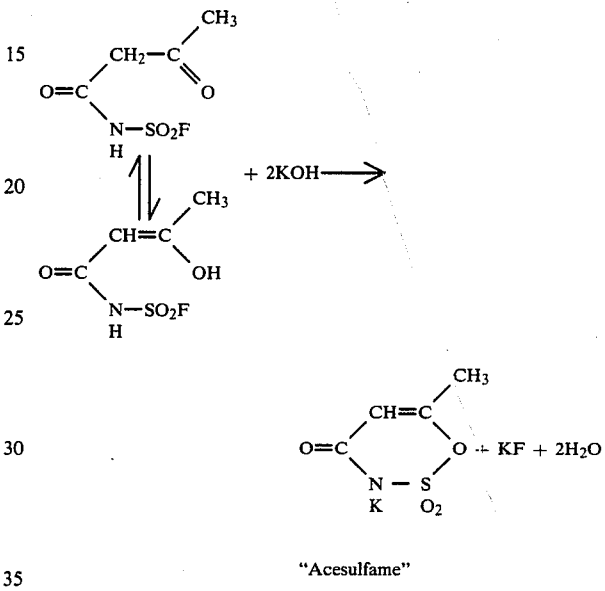

"Acesulfame"

Although some of the known processes provide quite satisfactory yields of 6-methyl 3,4-dihydro-1,2,3-oxathiazin-4 one 2,2-dioxide and its non-toxic salts (up to about 85% of theory based on the starting sulfamoyl halide), they are still in need of improvement, particularly for industrial purposes, because of the necessity of using chloro- or fluorosulfonyl isocyanate, which are not very easy to obtain, as starting materials; this is because the preparation of the chloro- and fluorosulfonyl isocyanate requires considerable precautionary measures and safety arrangements by reason of the starting materials (HCN, Cl₂, SO₃ and HF), some of which are rather unpleasant to handle. The preparation of the chloro- and fluorosulfonyl isocyanate are based on the following reaction equations:

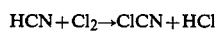
HCN+Cl₂→ClCN+HCl

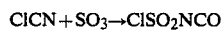
ClCN+SO₃→ClSO₂NCO

ClSO₂NCO+HF→FSO₂NCO+HCl

Replacement of the sulfamoyl fluoride in the process according to the abovementioned German Offenlegungsschrift No. 2,453,063 by, for example, the considerably more easily obtainable (for example from NH₃+SO₃) sulfamic acid H₂NSO₃H or its salts hardly appeared promising because the reaction of Na sulfamate H₂NSO₃Na with diketene in an aqueous-alkaline solution does not provide any reaction product which can be isolated pure. Rather, it has been possible to obtain the 1:1 adduct, which is probably at least partially formed in this reaction, only in the form of the coupling product with 4-nitrophenyldiazonium chloride, as a pale yellow dyestuff; see Ber. 83 (1950), pages 551–558, in particular page 555, last paragraph before the description of the experiments, and page 558, last paragraph:

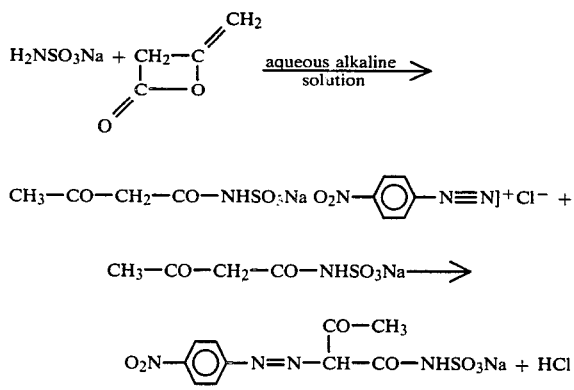

Moreover, the acetoacetamide-N-sulfonic acid has otherwise been postulated only, or also, as an intermediate in the decomposition of 6-methyl-3,4-dihydro-1,2,3-oxathiazin-4-one, 2,2-dioxide during boiling in aqueous solution; see the literature cited in the introduction, Angew. Chemie (1973) loc. cit.:

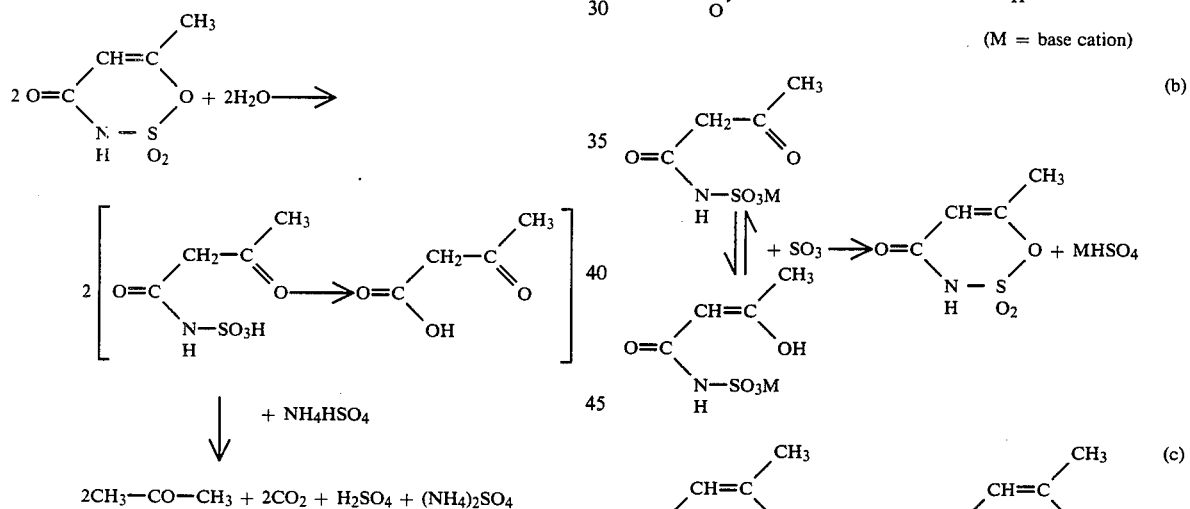

Thus, because the state of the art processes for the preparation of 6-methyl-3,4-dihydro-1,2,3-oxathiazin-4-one 2,2-dioxide and its non-toxic salts are, in particular, not entirely satisfactory for being carried out on an industrial scale, in particular as a result of the necessity to use starting materials which are not very straight-forward to obtain, the object was to improve the known processes appropriately or to develop a new improved process.

This object has been achieved according to the invention by a modification of the process of German Offenlegungsschrift No. 2,453,063 (mainly replacement of the sulfamoyl fluoride in the known process by salts of sulfamic acid) followed by ring closure of the resulting acetoacetylation product using $SO_3$.

Thus, the invention relates to a process for the preparation of 6-methyl-3,4-dihydro-1,2,3-oxathiazin-4-one 2,2-dioxide and its non-toxic salts by (a) reaction of a sulfamic acid derivative with at least an approximately equimolar amount of an acetoacetylating agent in an inert organic solvent, where appropriate in the presence of an amine or phosphine catalyst, to give an acetoacetamide derivative and (b) ring closure of the acetoacetamide derivative;

the process comprises the use as the sulfamic acid derivative in step (a) of a salt of sulfamic acid which is at least partially soluble in the inert organic solvent used, the ring closure in step (b) of acetoacetamide-N-sulfonate or of the free acetoacetamide-N-sulfonic acid, which is formed in the first step, by the action of at least an approximately equimolar amount of $SO_3$, where appropriate in an inert inorganic or organic solvent, to form the ring of 6-methyl-3,4-dihydro-1,2,3-oxathiazin-4-one 2,2-dioxide, and then the neutralization with a base of the product which results from this in the acid form, where appropriate in an additional step (c).

The reaction equations on which the process is based are as follows (with diketene as the acetoacetylating agent):

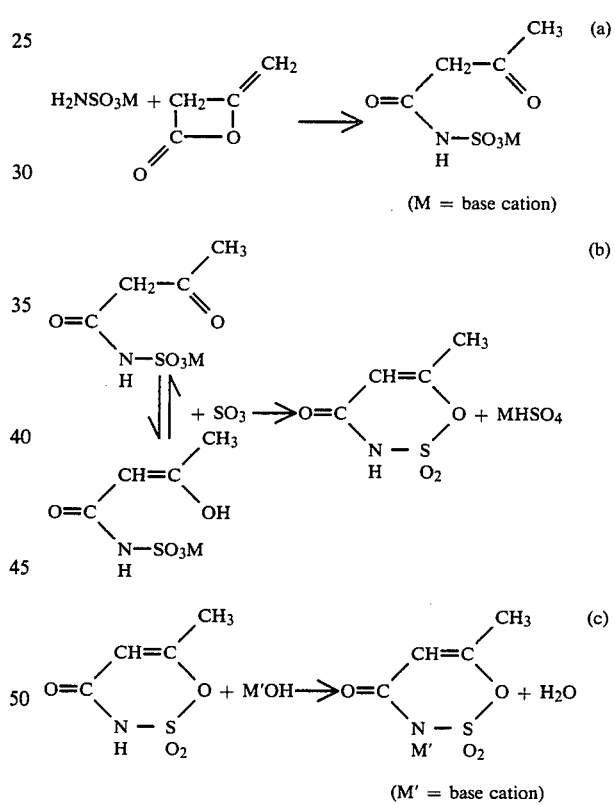

The process starts from starting materials which are straightforward to obtain and of low cost and it is extremely straightforward to carry out. The yields are
about 90 to 100% of theory in step (a) (based on the starting sulfamate),
about 70 to 95% of theory in step (b) (based on the acetoacetamide-N-sulfonate) and
about 100% of theory in step (c) (based on the oxathiazinone in the acid form),
so that the yields resulting for the overall process are between about 65 and 95% theory. Thus, compared with the state of the art processes, the invention represents a considerable advance.

It is extremely surprising that the reaction between sulfamate and acetoacetylating agent to give acetoacetamide-N-sulfonate by step (a) takes place smoothly because, on the basis of literature reference Ber. 83 (1950) loc. cit., according to which the reaction between Na sulfamate and diketene in aqueous-alkaline solution is apparently only rather undefined, a good yield and a 1:1 reaction product, which could be isolated pure without difficulty, was hardly to be expected from sulfamic acid or its salts and acetoacetylating agents.

It is equally surprising that the ring closure of acetoacetamide-N-sulfonate or of the free sulfonic acid, using $SO_3$ in step (b) of the process, takes place exceedingly well, because the elimination of water or bases (MOH) taking place with ring closure in this step either does not occur or, at any rate, virtually does not occur with other agents which eliminate water or bases, such as, for example, $P_2O_5$, acetic anhydride, trifluoroacetic anhydride, thionyl chloride etc.

In detail, the process according to the invention is carried out as follows:

Step (a):

It is possible to use as the acetoacetylating agent the compounds known for acetoacetylations such as, for example, acetoacetyl chloride and diketene; the preferred acetoacetylating agent is diketene.

The amount of acetoacetylating agent used should be at least approximately equimolar (related to the reactant sulfamate). It is preferable to use an excess of up to about 30 mol-%, in particular an excess of only up to about 10 mol-%. Excesses greater than about 30 mol-% are possible, but entail no advantage.

Suitable inert organic solvents are virtually all organic solvents which do not react in an undesired manner with the starting materials and final products or, where appropriate, the catalysts in the reaction, and which also have the ability to dissolve, at least partially, salts of sulfamic acid. Thus, the following organic solvents may be mentioned in this context as suitable and preferred:

halogenated aliphated hydrocarbons, preferably those having up to 4 carbon atoms such as, for example, methylene chloride, chloroform, 1,2-dichloroethane, trichloroethylene, tetrachloroethylene, trichlorofluoroethylene etc.;

aliphatic ketones, preferably those having 3 to 6 carbon atoms such as, for example, acetone, methyl ethyl ketone etc.;

aliphatic ethers, preferably cyclic aliphatic ethers having 4 or 5 carbon atoms such as, for example, tetrahydrofuran, dioxane etc.;

lower aliphatic carboxylic acids, preferably those having 2 to 6 carbon atoms such as, for example, acetic acid, propionic acid etc.;

aliphatic nitriles, preferably acetonitrile;

N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone etc.;

aliphatic sulfoxides, preferably dimethyl sulfoxide, and aliphatic sulfones, preferably sulfolane

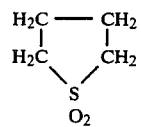

Particularly preferred solvents from the above list are methylene chloride, 1,2-dichloroethane, acetone, glacial acetic acid and dimethylformamide, especially methylene chloride.

The solvents can be used either alone or in a mixture.

The ratio of the amounts of the reaction starting materials to the solvent can vary within wide limits; in general, the weight ratio is about 1:(2–10). However, other ratios are also possible.

In principle, the amine and phosphine catalysts which can be used are all amines and phosphines whose use as catalysts for addition reactions of diketene is known. These are mainly tertiary amines and phosphines (still) having nucleophilic characteristics.

Those which are preferred in the present case are tertiary amines and phosphines in which each N or P atom has up to 20, in particular only up to 10, carbon atoms. The following tertiary amines may be mentioned as examples:

Trimethylamine, triethylamine, tri-n-propylamine, triisopropylamine, tri-n-butylamine, triisobutylamine, tricyclohexylamine, ethyldiisopropylamine, ethyldicyclohexylamine, N,N-dimethylaniline, N,N-diethylaniline, benzyldimethylamine, pyridine, substituted pyridines, such as picolines, lutidines, collidines or methyl ethyl pyridines, N-methylpiperidine, N-ethylpiperidine, N-methylmorpholine, N,N'-dimethylpiperazine, 1,5-diazabicyclo[4.3.0]non-5-ene, 1,8-diazabicyclo[5.4.0]undec-7-ene, also tetramethylhexamethylenediamine, tetramethylethylenediamine, tetramethylpropylenediamine, tetramethylbutylenediamine, as well as 1,2-dimorpholylethane, pentamethyldiethylenetriamine, pentaethyldiethylenetriamine, pentamethyldipropylenetriamine, tetramethyldiaminomethane, tetrapropyldiaminomethane, hexamethyltriethylenetetramine, hexamethyltripropylenetetramine, diisobutylenetriamine or triisopropylenetetramine.

A particularly preferred amine is triethylamine.

Examples of tertiary phosphines are methyldiphenylphosphine, triphenylphosphine, tributylphosphine etc.

The amount of catalyst is normally up to about 0.1 mole per mole of sulfamate. Larger amounts are possible, but entail hardly any advantages. In principle, reaction step (a) of the process according to the invention also takes place without catalyst; however, the catalyst acts to accelerate the reaction and is thus advantageous.

The sulfamic acid salts to be used for the process must be at least partially soluble in the inert organic solvent. This requirement is met by, preferably, lithium, $NH_4$ and the primary, secondary, tertiary and quaternary ammonium salts of sulfamic acid. In turn, the ammonium salts which are preferred are those whose ammonium ion contains not more than about 20, in particular not more than about 10, carbon atoms. Examples of ammonium salts of sulfamic acid are the salts having the following ammonium ions:

$N^{\oplus}H_4$, $H_3N^{\oplus}(C_2H_5)$, $H_2N^{\oplus}(n{-}C_3H_7)_2$, $H_2N^{\oplus}(i{-}C_3H_7)_2$ $HN^{\oplus}(CH_3)_3$, $HN^{\oplus}(C_2H_5)_3$, $HN^{\oplus}(n{-}C_3H_7)_3$, $HN^{\oplus}(n{-}C_4H_9)_3$, HN⊕(CH₃)₂CH₂C₆H₅, HN⊕(CH₃)₂(C₆H₅), N⊕(CH₃)₄, N⊕(C₂H₅)₄, N⊕(CH₃)₃C₆H₅ etc.

A particularly preferred sulfamate is the triethylammonium salt.

The salts are usually obtained in a manner known per se by neutralization of sulfamic acid with LiOH, NH₃ or the appropriate amines or quaternary ammonium hydroxide solutions, followed by removal of water. The base is preferably added in a stoichiometric excess (based on the sulfamic acid) of up to about 30 mol-%, in particular up to only about 15 mol-%. In addition, it is also preferred for the organic moiety in the ammonium ion to be identical to the organic moiety in the amine catalyst (for example use of triethylammonium sulfamate as the sulfamic acid salt and of triethylamine as the catalyst). In the case of salts with NH₃ and primary and secondary amines, a stoichiometric amount of the amine component is preferably used, and the catalyst added is a weakly basic tert.-amine, such as, for example, pyridine.

In general, the reaction temperature is selected to be in a range between about $-30°$ and $+50°$ C., preferably between about $0°$ and $25°$ C.

The reaction is normally carried out under atmospheric pressure. The reaction time can vary within wide limits; in general, it is between about 0.5 and 12 hours. The reaction can be carried out either by initial introduction of the sulfamic acid salt and metering in of diketene, or by initial introduction of diketene and metering in of the sulfamic acid salt, or by initial introduction of diketene and sulfamic acid and metering in of the base or, for example, by metering into the reaction chamber both reactants simultaneously, it being possible for the inert organic solvent either also to be initially introduced or to be metered in together with the reactants.

After the reaction is complete, for the isolation of the reaction product the solvent is removed by distillation and the residue (mainly acetoacetamide-N-sulfonate) is recrystallised from a suitable solvent such as, for example, acetone, methyl acetate or ethanol. The yields are about 90 to 100% of theory.

The Li and ammonium acetoacetamide-N-sulfonates are new compounds. They have the formula

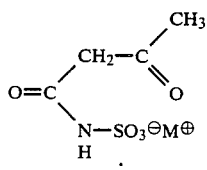

in which $M^⊕ = Li^⊕$ or $N^⊕R^1R^2R^3R^4$ with $R^1$, $R^2$, $R^3$ and $R^4$, independently of one another, being H or organic radicals, preferably H or $C_1-C_8$-alkyl, $C_6-C_{10}$-cycloalkyl, -aryl and/or -aralkyl.

The total number of carbon atoms in the ammonium ion in the ammonium salts is preferably not more than about 20, in particular not more than about 10.

The free acetoacetamide-N-sulfonic acid can, if desired, be obtained from the acetoacetamide-N-sulfonate by customary processes.

Step (b):

The acetoacetamide-N-sulfonate (or, where appropriate, the free acid) obtained in step (a) is then cyclized in step (b) using at least an approximately equimolar amount of SO₃, where appropriate in an inert inorganic or organic solvent. The SO₃ is generally used in an up to about 20-fold, preferably about 3- to 10-fold, in particular about 4- to 7-fold, molar excess based on the acetoacetamide-N-sulfonate (or the free acid). It can be added to the reaction mixture either in the solid or the liquid form or by condensing in SO₃ vapor. Normally however, a solution of SO₃ in concentrated sulfuric acid, liquid SO₂ or an inert organic solvent is used. It is also possible to use compounds which eliminate SO₃.

Although, in principle, it is possible to carry out the reaction without solvent, nevertheless it is preferable to carry out in an inert inorganic or organic solvent. Suitable inert inorganic or organic solvents are those liquids which do not react in an undesired manner with SO₃ or the starting materials or final products of the reaction. Thus, because of the considerable reactivity of, in particular, SO₃, only relatively few solvents are suitable for this purpose. Preferred solvents are:

Inorganic solvents: liquid SO₂;

organic solvents: halogenated aliphatic hydrocarbons, preferably having up to 4 carbon atoms, such as, for example, methylene chloride, chloroform, 1,2-dichloroethane, trichloroethylene, tetrachloroethylene, trichlorofluoroethylene etc.;

esters of carbonic acid with lower aliphatic alcohols, preferably with methanol or ethanol;

nitroalkanes, preferably having up to 4 carbon atoms, in particular nitromethane;

alkyl-substituted pyridines, preferably collidine; and aliphatic sulfones, preferably sulfolane.

It is possible to use the organic solvents either alone or in a mixture.

Particularly preferred solvents are liquid SO₂ and methylene chloride.

The amount of inert solvent used is not critical. When a solvent is used, it is merely necessary to ensure adequate solution of the reactants; the upper limit of the amount of solvent is determined by economic considerations.

In a preferred embodiment of the process according to the invention the same solvent is used in both step (a) and step (b); this is preferably a halogenated aliphatic hydrocarbon, in particular methylene chloride. This is because, in this case, the solution obtained in step (a) can, without isolation of the acetoacetamide-N-sulfonate, be used immediately for step (b).

The reaction temperature in step (b) is normally between about $-70°$ and $+175°$ C., preferably between about $-40°$ and $+10°$ C.

Step (b) resembles step (a) in that it is normally carried out only under atmospheric pressure.

The reaction time can be up to about 10 hours.

The reaction can be carried out in such a manner that the acetoacetamide-N-sulfonate (or the free acid) is, where appropriate in solution, introduced and SO₃, where appropriate in the dissolved form, is metered in, or both reactants are simultaneously transferred into the reaction chamber, or SO₃ is initially introduced and the acetoacetamide-N-sulfonate (or the free acid) is added.

It is preferable initially to introduce part of the SO₃, where appropriate in solution, and then to meter in, either continuously or in portions, acetoacetamide-N-sulfonate (or the free acid) and SO₃, where appropriate in the dissolved form.

Working-up is carried out in a customary manner. In the preferred case where methylene chloride is used as the reaction medium, working-up can be carried out as follows, for example: to the solution containing SO₃ are added about 10 times the molar amount (based on SO₃) of ice or water. This brings about phase separation: the 6-methyl-3,4-dihydro-1,2,3-oxathiazin-4-one 2,2-dioxide which has formed is present mainly in the organic phase. The fractions still present in the aqueous sulfuric acid can be obtained by extraction with an organic solvent such as, for example, methylene chloride or an organic ester.

Otherwise, after the addition of water, the reaction solvent is removed by distillation, and the 6-methyl-3,4-dihydro-1,2,3-oxathiazin-4-one 2,2-dioxide which remains in the sulfuric acid of reaction is extracted with a more suitable solvent. Suitable solvents are those which are sufficiently stable towards sulfuric acid and which have a satisfactory dissolving capacity; in addition, the reaction product should have in the solvent system a partition coefficient which is favorable for the isolation. Not only halogenated hydrocarbons but also esters of carbonic acid such as, for example dimethyl carbonate, diethyl carbonate and ethylene carbonate, or esters of organic monocarboxylic acids such as, for example, isopropyl formate and isobutyl formate, ethyl acetate, isopropyl acetate, butyl acetate, isobutyl acetate and neopentyl acetate, or esters of dicarboxylic acids or amides which are immiscible with water, such as, for example, tetrabutylurea, are suitable. Isopropyl acetate and isobutyl acetate are particularly preferred.

The combined organic phases are dried with, for example, Na₂SO₄, and are evaporated. Any sulfuric acid which has been carried over in the extraction can be removed by appropriate addition of aqueous alkali to the organic phase. For this purpose, dilute aqueous alkali is added to the organic phase until the pH reached in the aqueous phase is that shown by pure 6-methyl-3,4-dihydro-1,2,3-oxathiazin-4-one 2,2-dioxide at the same concentration in the same two-phase system of extracting agent and water. When it is intended to obtain the free compound, this undergoes additional purification in a customary manner (preferably by recrystallization). The yield is between about 70 and 95% of theory based on acetoacetamide-N-sulfonate (or the free acid).

If, however, it is intended to obtain a non-toxic salt of 6-methyl-3,4-dihydro-1,2,3-oxathiazin-4-one 2,2-dioxide, neutralization step (c) is also carried out.

For this purpose, the oxathiazinone compound produced in the acid form in step (b) is neutralized with an appropriate base in a customary manner. With this in view, for example the organic phases which have been combined, dried and evaporated at the end of step (b) are neutralized in suitable organic solvents such as, for example, alcohols, ketones, esters or ethers, or in water, using an appropriate base, preferably using a potassium base such as, for example, KOH, KHCO₃, K₂CO₃, K alcoholates etc. Alternatively, the oxathiazinone compound is neutralized and extracted directly from the purified organic extraction phase (step (b) using an aqueous potassium base. The oxathiazinone salt then precipitates out, where appropriate after evaporation of the solution, in the crystalline form, and it can also be recrystallized for purification.

The yield in the neutralization step is virtually 100%.

Both the overall process according to the invention, consisting of process steps (a), (b) and (c), and the individual process steps (a) and (b) are new and considerably advantageous.

The Examples which follow are intended to illustrate the invention further. The (invention) examples of carrying out process steps (a), (b) and (c) are followed by a comparison example which shows that acetoacetamide-N-sulfonates do not cyclize with agents which eliminate water or bases other than SO₃, in this case P₂O₅.

(A) Examples of carrying out process step (a):

EXAMPLE 1

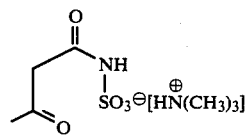

trimethylammonium acetoacetamide-N-sulfonate 9.7 g (0.1 mol) of sulfamic acid were added to a solution of 12 ml (0.125 mol) of trimethylamine in 100 ml of glacial acetic acid, and the mixture was stirred until dissolution was complete. Then, 8 ml (0.104 mol) of diketene were added dropwise, while cooling at 25°–30°. After 16 hours, the reaction product was precipitated by slow addition of ether and was filtered off with suction. 22 g (92%), melting point 101° C.

NMR (DMSO d₆) δ

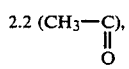

2.8 (N⊕—CH₃), 3.45 (—CH₂).
IR (KBr) 1045, 1240, 1470, 1660, 1720 cm⁻¹.

EXAMPLE 2

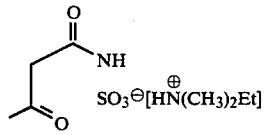

dimethylethylammonium acetoacetamide-N-sulfonate 80 g (1.096 mol) of dimethylethylamine were added dropwise, with cooling, to 80 g (0.825 mol) of sulfamic acid suspended in 500 ml of glacial acetic acid. When dissolution was complete, 80 ml (1.038 mol) of diketene were added, while cooling at 25°–35° C. After 16 hours, the mixture was evaporated and the residue was stirred with acetone, whereupon crystallization took place. 110 g (43%), melting point 73°–75° C.

The remainder of the reaction product, 128 g (50%), was obtained as a syrup from the mother liquor.

NMR (CDCl₃) 1.35 (CH₃)

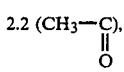

2.8 (N⊕—CH₃),

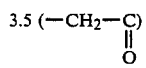

IR (KBr) 1050, 1240, 1475, 1690, 1730 cm⁻¹.

EXAMPLE 3

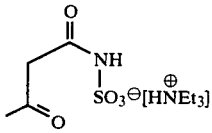

triethylammonium acetoacetamide-N-sulfonate 9.7 g (0.1 mol) of sulfamic acid in 100 ml of methylene chloride were induced to dissolve with 16 ml (0.12 mol) of triethylamine. Then, at 0° C., 8 ml (0.104 mol) of diketene were added dropwise. Stirring was continued at 0° C. for 2 hours and at room temperature for 2 hours. Then, the reaction product was precipitated by addition of hexane, and the remaining syrup was washed with more hexane. 27–28 g (95.7–99%) remained after drying in vacuo; the syrup began to crystallize after prolonged standing.

NMR (CDCl$_3$) δ1.33 (—CH$_3$), 2.2 (CH$_3$—C),
         ‖
         O 3.2 (N—CH$_2$),

O
              ‖
3.5 (—CH$_2$—C)

IR (neat) 1040, 1230, 1450, 1650, 1670 cm$^{-1}$.

The following Examples 4–7 were carried out in a manner analogous to that of Example 3; the result was:

EXAMPLE 4

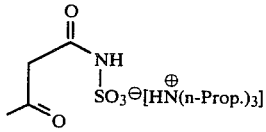

tri(n-propyl)ammonium acetoacetamide-N-sulfonate

Yield: 92–97%.
NMR (CDCl$_3$)δ

2.3 (—CH$_3$—C), 3.6 (—CH$_2$—C)
        ‖                ‖
        O                O

IR (CH$_2$Cl$_2$) 1040, 1260, 1420, 1700, 1740 cm$^{-1}$.

EXAMPLE 5

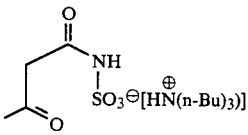

tri(n-butyl)ammonium acetoacetamide-N-sulfonate

Yield: 91–96%.
NMR (CDCl$_3$)δ

2.25 (CH$_3$—C), 3.5 (—CH$_2$—C)
       ‖                ‖
       O                O

IR (CH$_2$Cl$_2$) 1040, 1250, 1420, 1700, 1740 cm$^{-1}$.

EXAMPLE 6

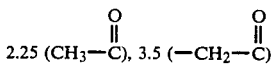

dimethylbenzylammonium acetoacetamide-n-sulfonate

Yield: 92–97%.
NMR (CDCl$_3$)δ2.2 (COCH$_3$), 2.75 (N⊕—CH$_3$), 3.5 (—CH$_2$—C),
           ‖
           O 4.3 (N⊕—CH$_2$—Ar), 7.35 (Ar).
IR (CH$_2$Cl$_2$) 1040, 1260, 1270, 1430, 1470, 1700, 1740 cm$^{-1}$.

EXAMPLE 7

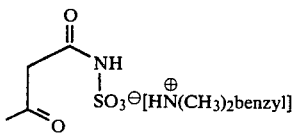

diisopropylethylammonium
acetoacetamide-N-sulfonate

Yield: 91–95%.
NMR (CDCl$_3$)δ1.3 and 1.4 (—CH$_3$), 2.2 (COCH$_3$), 3.5 L (CH$_2$—CO).
IR (CH$_2$Cl$_2$) 1040, 1210, 1250, 1420, 1700, 1740 cm$^{-1}$.

EXAMPLE 8

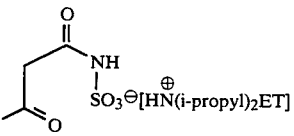

triethylammonium acetoacetamide-N-sulfonate 9.7 g (0.1 mol) of sulfamic acid were suspended in 100 ml of acetone, and 16 ml (0.12 mol) of triethylamine were added. When dissolution was almost complete, 8 ml (0.104 mol) of diketene were added dropwise at 0° C. Then, reaction was allowed to go to completion while stirring at room temperature, during which everything dissolved. After 16 hours, the reaction product was precipitated as a syrup using hexane, and the syrup was further purified by stirring with hexane. 27–28 g (95.7–99%) of syrup remained after drying in vacuo, and this slowly crystallized on standing.

NMR (CDCl$_3$)δ2.3 (—CH$_3$),

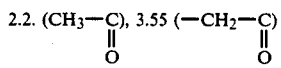

IR (neat) 1040, 1230, 1450, 1670 cm⁻¹.

EXAMPLE 9

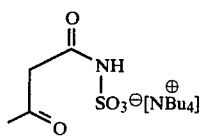

tetrabutylammonium acetoacetamide-N-sulfonate 105 ml (0.16 mol) of a 40% strength aqueous solution of tetrabutylammonium hydroxide were added to 15.5 g (0.16 mol) of sulfamic acid in 10 ml of methanol and 50 ml of water. The mixture was then evaporated to dryness. The residue was dissolved in 100 ml of methylene chloride, and the pH was adjusted to 9–10 with triethylamine. 10 ml of diketene were then added dropwise. After 12 hours, the pH was again adjusted to 9–10, and the addition of diketene was repeated. 16 hours later, the mixture was evaporated, whereupon the residue crystallized. The paste of crystals was filtered off with suction and washed with ethyl acetate and ether.

34.6 g (52%) melting point: 97°–98° C.

NMR (CDCl₃) δ1.33 (—CH₃), 2.2 (COCH₃),

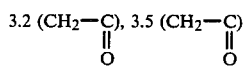

IR (CH₂Cl₂) 890, 1040, 1255, 1410 cm⁻¹.

EXAMPLE 10

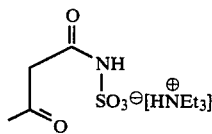

triethylammonium acetoacetamide-N-sulfonate 19.4 g (0.2 mol) of sulfamic acid and 15.4 ml (0.2 mol) of diketene in 200 ml of methylene chloride were initially introduced at 0° C. While cooling and stirring, 29 ml (0.21 mol) of triethylamine were added dropwise within 45 min. The reaction mixture was subsequently stirred at 0° C. for 30 min. and then allowed to stand overnight at room temperature. After evaporating off the solvent and drying in vacuo, the reaction product was obtained as a syrup. It was crystallized from acetone. 53–56 g (94–99%); melting point 55°–58° C.

NMR (CDCl₃) δ1.33 (—CH₃),

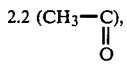

3.2 (N—CH₂),

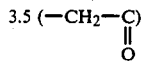

IR (neat) 1040, 1230, 1450, 1670 cm⁻¹.

EXAMPLE 11

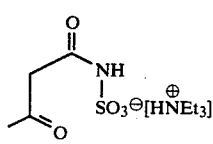

triethylammonium acetoacetamide-N-sulfonate 19.4 g (0.2 mol) of sulfamic acid, 15.4 ml (0.2 mol) of diketene and 1.14 ml (0.02 mol) of glacial acetic acid in 100 ml of methylene chloride were initially introduced at 0° C. While cooling and stirring, 29 ml (0.21 mol) of triethylamine were added dropwise within 45 min. The reaction mixture was subsequently stirred at 0° C. for 30 min. and then allowed to stand overnight at room temperature. After evaporating off the solvent, the residue was washed with diethyl ether and then dried in vacuo. It was crystallized from acetone.

52–5 g (92–97.5%) melting point 55°–58° C.

NMR (CDCl₃) δ1.33 (—CH₃),

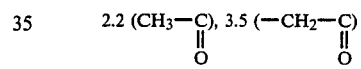

IR (neat) 1040, 1230, 1450, 1670 cm⁻¹.

EXAMPLE 12

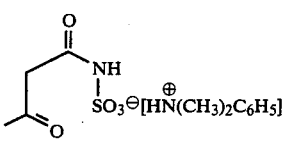

dimethylphenylammonium acetoacetamide-N-sulfonate 15.1 ml (120 mmol) of N,N-dimethylaniline were added to 9.7 g (100 mmol) of sulfamic acid in 100 ml of glacial acetic acid, and the mixture was stirred until dissolution was complete. 8 ml (104 mmol) of diketene were then added. After 16 hours, a further 2 ml of diketene were added to the solution. When the diketene had disappeared, the mixture was evaporated and the product was precipitated by stirring with ether.

Yield: 88–92%.

NMR (CDCl₃) δ2.2 (COCH₃),

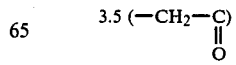

IR (CH₂Cl₂) 1040, 1250, 1430, 1700, 1740 cm⁻¹.

EXAMPLE 13

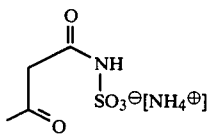

ammonium acetoacetamide-N-sulfonate 10 ml of diketene and 1 ml of pyrridine were added to a suspension of 11.4 g (100 mmol) of ammonium sulfamate in 100 ml of glacial acetic acid, while stirring vigorously. After 17 hours, the final product was filtered off with suction.

17 g=86%, decomposition above about 125° C.

EXAMPLE 14

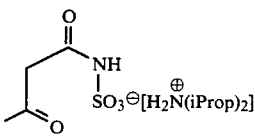

diisopropylammonium acetoacetamide-N-sulfonate 19.4 g (0.2 mol) of sulfamic acid in 200 ml of $CH_2Cl_2$ were neutralized with 28 ml (0.2 mol) of diisopropylamine. After addition of 0.81 ml (10 mmol) of pyridine, 15.4 ml (0.2 mol) of diketene were added dropwise at 0° C. The reaction mixture was subsequently stirred at 0° C. for 30 minutes and then allowed to stand overnight at room temperature. After evaporating off the solvent and drying in vacuo, the reaction product was obtained as a syrup.

45–48 g=80–85%.

IR (neat) 1040, 1280, 1450, 1670 $cm^{-1}$.

EXAMPLE 15

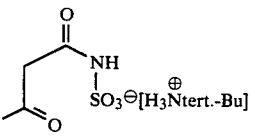

tert.-butylammonium acetoacetamide-N-sulfonate 19.4 g (0.2 mol) of sulfamic acid in 100 ml of DMF were neutralized with 21 ml (0.2 mol) tert.-butyl-amine. After addition of 0.81 ml (10 mmol) of pyridine, 15.4 ml (0.2 mol) of diketene were added dropwise at 15° C. The mixture was then stirred at room temperature for 3 hours. For working-up, the reaction product was precipitated with 500 ml of diethyl ether. For purification, the syrup was stirred with acetone.

Yield: 42 g=83%.

IR (neat) 1035, 1230, 1450, 1670 $cm^{-1}$.

(B) Examples of carrying out process steps (b) and (c):

EXAMPLE 1

12.7 g (50 mmol) of dimethylethylammonium acetoacetamide-N-sulfonate in 110 ml of methylene chloride were added dropwise to 8 ml (200 mmol) of liquid $SO_3$ in 100 ml of $CH_2Cl_2$ at −30° C., stirring vigorously, within 60 minutes. 30 minutes later, 50 ml of ethyl acetate and 50 g of ice were added to the solution. The organic phase was separated off, and the aqueous phase was extracted twice more with ethyl acetate. The combined organic phases were dried over sodium sulfate, evaporated and the residue was dissolved in methanol. On neutralization of the solution with methanolic KOH, the potassium salt of 6-methyl-3,4-dihydro-1,2,3-oxathiazin-4-one 2,2-dioxide precipitated out.

7.3 g=73%.

EXAMPLE 2

12.7 g (50 mmol) of dimethylethylammonium acetoacetamide-N-sulfonate in 110 ml of $CH_2Cl_2$ were added dropwise, within 60 minutes, to 8 ml (200 mmol) of liquid $SO_3$ in 50 ml of $SO_2$ at −30° C., stirring vigorously. 30 minutes later, after the evaporation of the $SO_2$, 50 ml of ethyl acetate and 50 g of ice were added to the solution. The organic phase was separated off, and the aqueous phase was extracted twice more with ethyl acetate. The combined organic phases were dried over sodium sulfate, evaporated and the residue was dissolved in methanol. On neutralization of the solution with methanolic KOH, the potassium salt of 6-methyl-3,4-dihydro-1,2,3-oxathiazin-4-one 2,2-dioxide precipitated out.

8.3 g=83%.

EXAMPLE 3

12.7 g (50 mmol) of dimethylethylammonium acetoacetamide-N-sulfonate in 110 ml of $CH_2Cl_2$ were added dropwise to 12 ml (300 mmol) of liquid $SO_3$ in 100 ml of $CH_2Cl_2$ at −30° C., stirring vigorously, within 60 minutes. 30 minutes later, 50 ml of ethyl acetate and 50 g of ice were added to the solution. The organic phase was separated off, and the aqueous phase was extracted twice more with ethyl acetate. The combined organic phases were dried over sodium sulfate, evaporated and the residue was dissolved in methanol. On neutralization of the solution with methanolic KOH, the potassium salt of 6-methyl-3,4-dihydro-1,2,3-oxathiazin-4-one 2,2-dioxide precipitated out.

7.6 g=76%.

EXAMPLE 4

4.24 g (16.7 mmol) of dimethylethylammonium acetoacetamide-N-sulfonate in 35 ml of $CH_2Cl_2$ were added dropwise within 20 minutes to 4 ml (100 mmol) of liquid $SO_3$ in 100 ml of $CH_2Cl_2$ at −30° C., stirring vigorously. Then 4 ml (100 mmol) of $SO_3$ were added to the solution, followed by another 4.24 g (16.7 mmol) of dimethylethylammonium acetoacetamide-N-sulfonate in 35 ml of $CH_2Cl_2$ added dropwise within 20 minutes at −30° C., stirring vigorously. The addition of 4 ml (100 mmol) of $SO_3$ was then repeated. Then, 4.24 g (16.6 mmol) of dimethylethyl-ammonium acetoacetamide-N-sulfonate in 35 ml of $CH_2Cl_2$ were added dropwise within 20 minutes at −30° C., stirring vigorously. 20 minutes later, the mixture was worked up as in Example 1.

8.7 g=87%.

EXAMPLE 5

12.7 g (50 mmol) of dimethylethylammonium acetoacetamide-N-sulfonate in 110 ml of $CH_2Cl_2$ were added dropwise within 60 minutes to 2.4 ml (60 mmol) of $SO_3$ in 100 ml of $CH_2Cl_2$ at −25° C., stirring vigorously. Over the same period, 2.4 ml (60 mmol) of $SO_3$ were added on each occasion after 12, 24, 36 and 48 minutes. 20 minutes later, the mixture was worked up as in Example 1.

8.8 g=88%.

EXAMPLE 6

The process was carried out as in Example 5, but 2.4 ml (60 mmol) of $SO_3$ in 50 ml of $SO_2$ were introduced at the start.

8.8 g=88%.

EXAMPLE 7

12.8 g (160 mmol) of solid $SO_3$ were dissolved in 150 ml of $CH_2Cl_2$. After the solution had been cooled to $-45°/-55°$ C., 8.4 g (26 mmol) of tripropylammonium acetoacetamide-N-sulfonate in 25 ml of $CH_2Cl_2$ were added dropwise within 60 minutes. After 4 hours at $-45°/-55°$ C., the mixture was worked up as in Example 1.

2.8 g=54%.

In Examples 8–12, the reaction solutions from the reaction of diketene, sulfamic acid and triethylamine were used directly.

EXAMPLE 8

125 ml of triethylammonium acetoacetamide-N-sulfonate solution (0.1 mol; $CH_2Cl_2$) were added dropwise, within 60 minutes, to 20 ml (500 mmol) of liquid $SO_3$ in 500 ml of $CH_2Cl_2$ at $-30°$ C., stirring vigorously. After a further 60 minutes at $-30°$ C., the mixture was worked up as in Example 1.

17.1 g=85%.

EXAMPLE 9

125 ml of triethylammonium acetoacetamide-N-sulfonate solution (0.1 mol; $CH_2Cl_2$) were initially introduced into 250 ml of $CH_2Cl_2$ at $-30°$ C. 20 ml (500 mmol) of liquid $SO_3$ dissolved in 250 ml of $CH_2Cl_2$ were added within 60 minutes. After a further 60 minutes at $-30°$ C., the mixture was worked up as in Example 1.

14.9 g=74%.

EXAMPLE 10

125 ml of triethylammonium acetoacetamide-N-sulfonate solution (0.1 mol; $CH_2Cl_2$) were added dropwise, within 60 minutes, to 4.8 ml (120 mmol) of liquid $SO_3$ in 500 ml of $CH_2Cl_2$ at $-25°$ C. Four more portions of 4.8 ml (120 mmol) of liquid $SO_3$ were added at intervals of 12 minutes. After another 60 minutes at $-25°$ C., the mixture was worked up as in Example 1.

18.3 g=91%.

EXAMPLE 11

50 ml of $CH_2Cl_2$ at $-30°$ C. were initially introduced. While cooling and stirring efficiently, a solution of 28.1 g (0.1 mol) of triethylammonium acetoacetamide-N-sulfonate in 50 ml of $CH_2Cl_2$, and 24 ml of liquid $SO_3$ in 50 ml of $CH_2Cl_2$, were simultaneously and steadily added dropwise within 30 min. After another 30 min at $-25°$ C. to $-30°$ C., 110 ml of water were cautiously added dropwise at the same temperature. The $CH_2Cl_2$ was then removed by distillation, and the reaction product was extracted with 80 ml of i-butyl acetate. 20 ml of water were then added to the organic phase and, while stirring vigorously, the pH was adjusted to 0.84–0.87 (pH meter, glass electrode:Ingold 405-60-S7) with 4 n KOH. After separation and extraction of the aqueous phase with 20 ml of i-butyl acetate, 15 ml of water were added to the combined i-butyl acetate phases and neutralized to pH 5–7 with 4 n KOH, while stirring. The partially precipitated K salt was filtered off with suction and then combined with the aqueous phase of the filtrate. Evaporation of the water in vacuo provided 18.1 g=90% of sweetener.

EXAMPLE 12

50 ml of $CH_2Cl_2$ at $-30°$ C. were initially introduced. Then a solution of 28.1 g (0.1 mol) of triethylammonium acetoacetamide-N-sulfonate in 50 ml of $CH_2Cl_2$, and 24 ml of liquid $SO_3$ in 50 ml of $CH_2Cl_2$, were simultaneously and steadily run in while cooling intensively (isopropanol/dry ice). Immediate working-up as in Example 11 (extractant: isopropyl acetate) provided 17.9 g=89% of sweetener.

EXAMPLE 13

12.4 ml of 60% oleum (200 mmol of $SO_3$) were initially introduced into 200 ml of $CH_2Cl_2$ at $-25°$ C. 62.5 ml of triethylammonium acetoacetamide-N-sulfonate solution (50 mmol; $CH_2Cl_2$) were added dropwise within 30 minutes. After a further 60 minutes at $-25°$ C., the mixture was worked up as in Example 1.

4.7 g=47%.

EXAMPLE 14

8 ml (200 mmol) of liquid $SO_3$ were cautiously added to 200 ml of collidine at $-30°$ C. Then 16.2 g (50 mmol) of tripropylammonium acetoacetamide-N-sulfonate were added, and the reaction mixture was heated at about 100° C. for 20 hours. Most of the collidine was then removed by distillation in vacuo, and the residue was taken up in ethyl acetate. After acidification with sulfuric acid, the aqueous phase was thoroughly extracted with ethyl acetate. The organic phases were dried over $Na_2SO_4$ and evaporated in vacuo. The residue was taken up in methanol and neutralized with methanolic potassium hydroxide solution. The precipitated sweetener was filtered off with suction and dried.

2.2 g=22%.

COMPARISON EXAMPLE 35.42 g (250 mmol) of $P_2O_5$ were initially introduced into 250 ml of $CH_2Cl_2$. At $-25°$ C., 62.5 ml of triethylammonium acetoacetamide-N-sulfonate solution in $CH_2Cl_2$, with a sulfonate content of 0.05 mol, were added dropwise within 60 minutes. After a further 60 minutes at $-25°$ C., the mixture was worked up as in Example B-1. No 6-methyl-3,4-dihydro-1,2,3-oxathiazin-4-one 2,2-dioxide or its potassium salt could be detected in the reaction product by thin-layer chromatography.

We claim:

1. A process for the preparation of 6-methyl-3,4-dihydro-1,2,3-oxathiazin-4-one-2,2-dioxide and its non-toxic salts which comprises:
   (a) reacting a sulfamic acid salt with at least an approximately equimolar amount of an acetoacetylating agent in an inert organic solvent, the sulfamic acid salt being at least partially soluble in the inert organic solvent, which reaction may be carried out in the presence of an amine or phosphine catalyst, to form an acetoacetamide-N-sulphonic acid salt, and
   (b) reacting the acetoacetamide-N-sulphonic acid salt with at least an approximately equimolar amount of SO₃, which reaction may be carried out in an inert inorganic or organic solvent, to form the ring of 6-methyl-3,4-dihydro-1,2,3-oxathiazin-4-on-2,2-dioxide.

2. The process of claim 1, further comprising
(c) neutralizing the 6-methyl-3,4-dihydro-1,2,3-oxathiazin-4-one-2,2-dioxide with a base to form a salt.

3. The process as claimed in claim 1, wherein diketene is used as the acetoacetylating agent in step (a).

4. The process as claimed in claim 1, wherein the acetoacetylating agent in step (a) is used in an excess of up to about 30 mol-%, preferably only up to about 10 mol-%.

5. The process as claimed in claim 1, wherein the inert organic solvent used in step (a) is a solvent from the following group, alone or in a mixture:
halogenated aliphatic hydrocarbons, preferably having up to 4 carbon atoms,
aliphatic ketones, preferably having 3 to 6 carbon atoms,
aliphatic ethers, preferably cyclic ethers having 4 or 5 carbon atoms,
lower aliphatic carboxylic acids, preferably having 2 to 6 carbon atoms,
lower aliphatic nitriles, preferably acetonitrile,
N-alkyl-substituted amides of carbonic acid and lower aliphatic carboxylic acids, preferably amides having a total of up to 5 carbon atoms,
aliphatic sulfoxides, preferably dimethyl sulfoxide, and
aliphatic sulfones, preferably sulfolane.

6. The process as claimed in claim 1, wherein the inert organic solvent used in step (a) is methylene chloride, 1,2-dichloroethane, acetone, glacial acetic acid and/or dimethylformamide, in particular methylene chloride.

7. The process as claimed in claim 1, wherein the amine or phosphine catalysts used in step (a) are nucleophilic tertiary amines and phosphines—preferably only amines—having up to 20—preferably up to only 10—carbon atoms per N or P atom, in particular triethylamine.

8. The process as claimed in claim 1, wherein the salts of sulfamic acid which are used in step (a) and are at least partially soluble in the inert organic solvent are the lithium, NH₄ and primary, secondary, tertiary and/or quaternary ammonium salts of sulfamic acid.

9. The process as claimed in claim 1, wherein step (a) is carried out at temperatures between about −30° and +50° C., preferably between about 0° and +25° C.

10. The process as claimed in claim 1, wherein the SO₃ in step (b) is used in a molar excess of up to about 20-fold, preferably about 3- to 10-fold, in particular 4- to 7-fold, relative to the acetoacetamide-N-sulfonate.

11. The process as claimed in claim 1, wherein the inert inorganic solvent used in step (b) is liquid SO₂, and the inert organic solvent used is at least one solvent from the following group:
halogenated aliphatic hydrocarbons, preferably having up to 4 carbon atoms,
esters of lower alcohols and carbonic acid, preferably methyl and ethyl carbonate,
lower nitroalkanes, preferably having up to 4 carbon atoms,
collidine and
sulfolane.

12. The process as claimed in claim 1, wherein the same inert solvent, preferably a halogenated aliphatic hydrocarbon, in particular methylene chloride, is used in both step (a) and step (b), and the solution obtained in step (a) is, without isolation of the acetoacetamide-N-sulfonate, transferred to the ring closure reaction of step (b).

13. The process as claimed in claim 1, wherein step (b) is carried out at temperatures between about −70° and +175° C., preferably between about −40° and +10° C.

14. The process as claimed in claim 1, wherein the base used in step (c) is a K base.

* * * * *